US010023896B2

United States Patent
Bain et al.

(10) Patent No.: US 10,023,896 B2
(45) Date of Patent: Jul. 17, 2018

(54) CUSHIONING DEVICE INSPECTION SYSTEM, A SAMPLING DEVICE FOR INSPECTION OF A CUSHIONING DEVICE AND A CUSHIONING DEVICE INSPECTION METHOD

(71) Applicant: PNEUMA PURE I.P. LIMITED, Dublin (IE)

(72) Inventors: Duncan Bain, Herts (GB); David Woolfson, Dalkey (IE)

(73) Assignee: Pneuma Pure Holdings Limited, Dublin (IE)

( * ) Notice: Subject to any disclaimer, the term of this patent is extended or adjusted under 35 U.S.C. 154(b) by 219 days.

(21) Appl. No.: 14/413,850

(22) PCT Filed: Jul. 10, 2013

(86) PCT No.: PCT/EP2013/064611
§ 371 (c)(1),
(2) Date: Jan. 9, 2015

(87) PCT Pub. No.: WO2014/009430
PCT Pub. Date: Jan. 16, 2014

(65) Prior Publication Data
US 2015/0176047 A1 Jun. 25, 2015

(30) Foreign Application Priority Data
Jul. 11, 2012 (GB) .................... 1212364.2

(51) Int. Cl.
*C12Q 1/04* (2006.01)
*G01N 1/22* (2006.01)
*A47C 31/00* (2006.01)

(52) U.S. Cl.
CPC .............. *C12Q 1/04* (2013.01); *A47C 31/007* (2013.01); *G01N 1/2226* (2013.01)

(58) Field of Classification Search
CPC ....... C12Q 1/04; A47C 31/007; G01N 1/2226
See application file for complete search history.

(56) References Cited

U.S. PATENT DOCUMENTS

| 3,903,915 A | 9/1975 | Rosaz |
| 4,678,014 A | 7/1987 | Owen |

(Continued)

FOREIGN PATENT DOCUMENTS

| CA | 2541341 | 9/2007 |
| CN | 2630530 | 8/2004 |

(Continued)

OTHER PUBLICATIONS

Machine Translation of DE4430150. Translated on Oct. 3, 2016.*

(Continued)

*Primary Examiner* — Michael L Hobbs
(74) *Attorney, Agent, or Firm* — Faegre Baker Daniels LLP

(57) ABSTRACT

A system for checking interior air contamination, the system including a sealed device including twin ports, a sampling device including a pump to extract at least some of the air from the interior of the sealed device, and a microbial detect to determine if the air contains contaminants. The twin ports are removably engageable with the sampling device to allow a circuit of air between the pump unit and the sealed device, such that air extracted from one of the twin ports by the pump is returned to the other of the twin ports, allowing no escape of the air to the environment. The sealed device is sealed to prevent, except through the twin ports, exterior air to flow into the sealed device and the air from the interior to flow out.

25 Claims, 11 Drawing Sheets

(56) References Cited

U.S. PATENT DOCUMENTS

| | | | |
|---|---|---|---|
| 4,766,628 A | 8/1988 | Walker | |
| 6,460,560 B1 | 10/2002 | Weinheimer | |
| 2003/0210994 A1 | 11/2003 | Boyd | |
| 2004/0107782 A1 | 6/2004 | Bradley | |
| 2004/0194561 A1 | 10/2004 | Aicher | |
| 2005/0046182 A1 | 3/2005 | Trapp | |
| 2006/0198741 A1 | 9/2006 | Wu | |
| 2008/0148624 A1* | 6/2008 | Borth | G01N 33/68 43/131 |
| 2012/0107157 A1 | 5/2012 | Tsai | |

FOREIGN PATENT DOCUMENTS

| | | | |
|---|---|---|---|
| CN | 101875901 | 11/2010 | |
| CN | 201836068 | 5/2011 | |
| DE | 4430150 | 10/1995 | |
| DE | 4430150 C1 * | 10/1995 | G01N 33/0011 |
| DE | 19849242 | 4/2000 | |
| DE | 202010008957 | 5/2011 | |
| JP | H08301358 | 11/1996 | |
| WO | WO 2011/061270 | 5/2011 | |

OTHER PUBLICATIONS

International Search Report issued by the International Searching Authority, dated Oct. 15, 2013, for related International Application No. PCT/EP2013/064611; 6 pages.

Search Report Under Section 17 issued by the Intellectual Property Office, dated Aug. 30, 2013, for related Application No. GB1212364.2; 4 pages.

Combined Search and Examination Report under Sections 17 and 18(3), dated Sep. 18, 2012, for related Application No. GB1212364.2; 6 pages.

* cited by examiner

CUSHIONING DEVICE INSPECTION SYSTEM, A SAMPLING DEVICE FOR INSPECTION OF A CUSHIONING DEVICE AND A CUSHIONING DEVICE INSPECTION METHOD

CROSS-REFERENCE TO RELATED APPLICATIONS

This application is a National Phase filing of International Application Serial No. PCT/EP2013/064611, filed Jul. 10, 2013, which claims the benefit of GB 1212364.2, filed Jul. 11, 2012; the disclosures of said applications are expressly incorporated herein by reference in their entirety.

BACKGROUND

In a hospital setting, cushioning devices in general, and in particular, mattresses, are typically provided with a waterproof cover to prevent soiling, and to allow wiping with cleaning and sterilising solutions. The waterproof cover may be a polymer sheet material or, more often, a fabric woven or knitted from polyamide or other suitable yarn, and then coated with a layer of occlusive material such as polyurethane. The knitted polyamide with polyurethane coating is frequently used to provide a degree of stretch, while providing water-proofing.

It is recognised in hospitals that these covers have a finite lifespan. Failure can occur in a number of ways: the waterproof coating can de-laminate from the knitted fabric, and possibly flake off. The complete material can be penetrated by stabbing or nicking with a sharp object. Seams can split or leak. Cleaning with inappropriate cleaning media can de-nature the waterproof coating, and render it permeable.

Failure of the waterproof cover has very undesirable consequences. Fluids, including body fluids containing pathogenic organisms, penetrate the mattress, where the typically foam interior retains the fluids like a sponge. The combination of a moist environment, contamination by body fluids and the pathogenic organisms contained therein, and warming by the body temperature of the patient lying on the mattress, create ideal conditions for the incubation and propagation of disease. Furthermore, as the patient moves on the mattress, or gets on or off the mattress, substantial quantities of air are blown in and out of the mattress interior. This air is often contaminated with aerosolised droplets of the contaminated fluids constituting a "microbial soup", contained in the mattress. This introduces a bio-hazard to the ambient atmosphere of the hospital ward. It also presents an extreme hazard of cross-infection between patients, as a succession of different patients occupy the same mattress.

These risks can be mitigated by regular visual inspection of the mattress interior, to observe if the waterproof cover has been pierced, torn or otherwise compromised. The inspection can involve hospital staff carrying out visual inspection and smelling the inside of the cover and exposed mattress area. If inspection indicates that the waterproof cover is not intact then there is consequential disposal of the mattress. To facilitate this inspection, mattresses are provided with a zip on the cover, and hospitals conduct regular inspections, referred to as audits, by un-zipping the cover to inspect inside the waterproof cover and the filling material.

However, this audit technique has a number of serious problems:

1) The zip is typically not waterproof or air-tight. The provision of a zip on the mattress therefore provides the opportunity for ingress of water, or ingress or egress of aerosolised pathogens. Flaps and other arrangements which are sometime provided to cover the zip, only partially obviate this problem; The flap, so that the cushioning device can "breathe" cannot be hermetically sealed over the zip and is typically left open along the lower side of the zip. The opening is susceptible to air and liquid borne pathogen ingress.

2) In the event that the mattress has a contaminated interior, the individual performing the audit is exposed to high levels of contamination in the process of un-zipping the waterproof cover and inspecting the area inside the cover; and 3) Un-zipping and opening the cover distributes contamination to the surrounding air.

The present invention seeks to alleviate the problems associated with the prior art.

It is to be understood, throughout this specification, that the term "cushioning device" refers to a mattress, pillow, duvet, cushion, or other padded or upholstered bedding, seating, or padding product.

Furthermore, it is to be understood that the sampling device for sampling air from inside of the cushioning device may be a hand-held device but is not limited to hand-held devices.

The present invention accordingly provides a system for checking the interior of hermetically sealed cushioning devices for contamination, comprising a hermetically sealed cushioning device having a sealable port adapted to allow extraction of air from interior of the cushioning device, and means adapted for extracting air from the interior of the cushioning device, and means for analysing said extracted air to determine if it contains contaminants.

Other features of the system of the present invention are included in the appended claims.

The system comprises a sampling device for extracting a sample of air from inside a sealed cushioning device, the device having a nozzle removably engageable with a port on the sealed cushioning device. Thus, the present invention has the advantage of providing an auditing system comprising the sampling device for sampling air from the interior of a cushioning device; and the sealable port adapted to be secured on the cushioning device.

The present invention also provides a cushioning device comprising a port adapted for connection to a cushioning device and removeably engageable with a sampling device. The invention also relates to a method for sampling air from the interior of a mattress by means of providing the mattress with a port through which air may be sampled, and using a pump or blower to extract air from said port for sampling; optionally the method includes the step of extracting air from the mattress to allow sampling of air from within the mattress core.

In one aspect, the present invention relates to a sampling device for extracting a sample of air from inside a sealed cushioning device, the device having a nozzle removeably engageable with a port on the sealed cushioning device.

In another aspect, the present invention provides a sealable port adapted for connection to a cushioning device and the sealable port being adapted to be removeably engageable with a sampling device, the port having means for attaching the port to the cushioning device; and the port having means for containing air within the cushioning device until such time as an inspection of the contents is carried out.

Conveniently, the sealable port may comprise a flanged tube attachable to a cover of a cushioning device and the means for attaching the port to the cushioning device may optionally, comprises the cover having a hole corresponding in size to the bore-hole of a flanged tube and the flanged tube being provided with means to secure the flanged tube in the hole.

In one embodiment a nut may be fed through the hole, exploiting the elastic nature of the cover material to allow its passage through the relatively small hole; the flanged tube defining the port has, a threaded section, and the flanged tube is fed through the hole; Once again exploiting the flexibility of the cover, the nut is then tightened to the port, trapping the boundary of the hole between the nut and the port.

Advantageously, at least one rubber gasket, is include in the assembly to aid sealing. Numerous existing technologies used for cable glands, for example, employ ratchets and other devices to ensure that the nut does not loosen. Alternatively, numerous adhesives and adhesive tapes are available attaching the port to the cover.

Alternatively, the cover may be conveniently punched with a hole and the means for attaching the port to the cushioning device comprises a die-cut disc of double-sided self-adhesive tape, also with a hole, placed over the hole in the cover whereby the port, is then affixed to the other side of the self-adhesive tape disc.

In another alternative embodiment, the means for attaching the sealable port to the cushioning device comprises welding.

Preferably, the sealable port comprises means for preventing flow of air in or out through the port when inspection is not taking place i.e. when the port is not in use for sampling air within the cushioning device.

Advantageously, the means for preventing flow of air in or out through the sealable port when inspection is not taking place, may comprise a removeable cap provided on the port to prevent ingress or egress of air, when inspection of the interior is not taking place.

Alternatively, the means for preventing flow of air may comprise any one of the following group: a pinch valve, a one way valve, a roll-over closure or similar means.

Conveniently, the cap comprises a threaded cap, which screws onto a corresponding thread on the port.

Ideally, a seal is provided within the cap to provide a seal when the cap is screwed tight; optionally wherein the seal comprises a rubber disc.

In a second aspect, the present invention provides a cushioning device for example, a mattress comprising a port adapted for connection to a cushioning device and removeably engageable with a sampling device.

Preferably, the cushioning device of the present invention may be provided with a first port and a second port, to allow a circuit of air between the sampling device, pump, or blower, and the cushioning device, such that air extracted from one port by the pump is returned to the other port, allowing no escape of potentially contaminated air to the ambient environment.

In a further aspect, the present invention provides a sampling device for extracting a sample of air from inside a sealed cushioning device, the device having a nozzle removeably engageably with a port on the sealed cushioning device.

Preferably, the sampling device for extracting a sample of air from inside a sealed cushioning device, comprises a casing, contains a blower unit comprising a motor, and a fan or impeller; optionally wherein the blower is powered by a battery unit, which may be contained within a handle, and activated by operating a switch; and optionally wherein a nozzle, mates with the mattress port. As previously described, suitable arrangements may readily be provided whereby the application of the nozzle to the port opens the port and allows air to flow.

In a further aspect, the present invention also provides a method for sampling air from the interior of a mattress comprising a device for sampling and a port securable to a cushioning device; the method comprising the following steps: providing the mattress with a port through which air may be sampled, and using a pump or blower to extract air from said port for sampling; optionally the method includes the step of extracting air from the mattress to allow sampling of air from within the mattress core.

Other features of the method of the present invention are included in the appended claims.

The method has the advantage that it enables the interior of a cushioning device such as mattress, pillow, duvet, cushion, or other padded or upholstered bedding, seating, or other padding product to be sampled and wherein the air from the cushioning device is tested for presence of bacteria, fungi or other microbes within the cushioning device.

Preferably, the presence of microbial activity is identified by measuring adenosine triphosphate, or other substances indicative of microbial life in the cushioning device.

Ideally, the cushioning device is sealed, by providing an occlusive cover and welded seams, allowing access via the port for sampling.

Most preferably, the sealed cushioning device is provided with a vent comprising a microbial filter to allow passage of air but no passage of microbes, to replenish air within the cushioning device and so facilitate extraction of air via the port.

Advantageously, the method includes the step of testing the air extracted from the cushioning device, by testing in real time, using an analyser to detect presence of microbes or chemical indicators of microbes.

Optionally, the method includes the step of storing air extracted from the cushioning device for later analysis using chemical analyser, or stored for later analysis using swabs and culture plates.

Optionally, the method includes the step of passing air extracted from the cushioning device over a collection swab for subsequent analysis.

Ideally, the method may include the step of passing the air exhausted from the pump or blower through a suitable filter to remove contaminants present in the sampled air, so preventing distribution of contaminants to the ambient environment.

The present invention has the advantage that it provides a means for carrying out a full inspection of the interior of a cushioning device such as a mattress interior without having to open the cushioning device cover. In turn, this makes it unnecessary to provide the cushioning device e.g. the mattress with a zip. Furthermore, the method of the present invention has the advantage that it will not expose the person inspecting the mattress or the surroundings, to biological hazard from the mattress interior. In addition, by making the auditing process considerably easier, quicker, and less hazardous, it makes more frequent inspections viable, thus catching compromised covers earlier, and thus spreading less infection.

The present invention will now be described more particularly with reference to the accompanying drawings in which are shown a number of embodiments of the sampling device, inspection system and the inspection method of the present invention.

Although the drawings show a mattress and the following description refers to a mattress, it is, of course, to be understood that the present invention can be applied to any cushioning device of which a mattress is merely an example.

Figure 1:
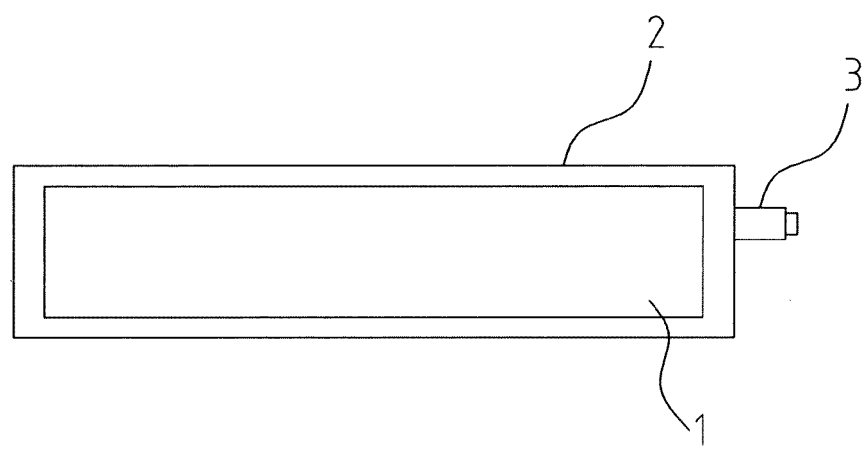
FIG. 1 is a side view of a mattress with an air sampling port provided thereon.

While the embodiments of the device, the port, the system and the method are shown by way of example in the drawings with reference to a mattress, it is, of course, to be understood that the present invention can be used in conjunction with any sealed cushioning device.

DESCRIPTION

Referring to FIG. 1, a mattress comprises a core, 1, a cover, 2, and a port, 3. The core of the mattress may be made of foam material such as polyurethane foam, visco foam, or other deformable material. The cover of the mattress may be knitted fabric coated with a waterproof material such as polyurethane. Alternatively, it may be a membrane material such as polyurethane sheet.

Figure 2:
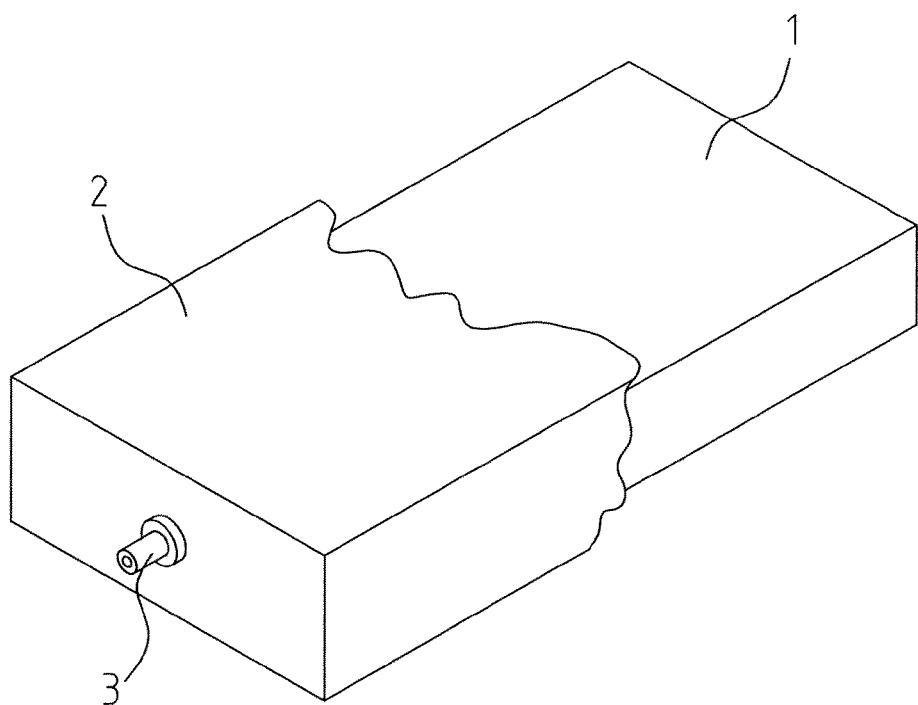
FIG. 2 is a perspective view of the mattress of FIG. 1 with the cover shown partially cut away.

FIG. 2 shows a perspective view, with the cover, 2, shown partially cut-away.

The mattress cover 2 is air-tight and waterproof, i.e. impermeable to liquids. The mattress cover 2 is preferably fabricated with welded seams so as to render the seams air-tight and waterproof.

Therefore, the only route for air to flow in or out of the mattress is via the port, 3. This means that for the air quality within the air to be sampled, it is not necessary to open or unzip the cover 2, but air may be sampled via the port 3. Even if the mattress has a zip, this still presents advantages over the currently known established inspection method of inspection which involves unzipping the cover, in the present invention, it is not necessary to unzip and expose the whole mattress.

Figure 3:
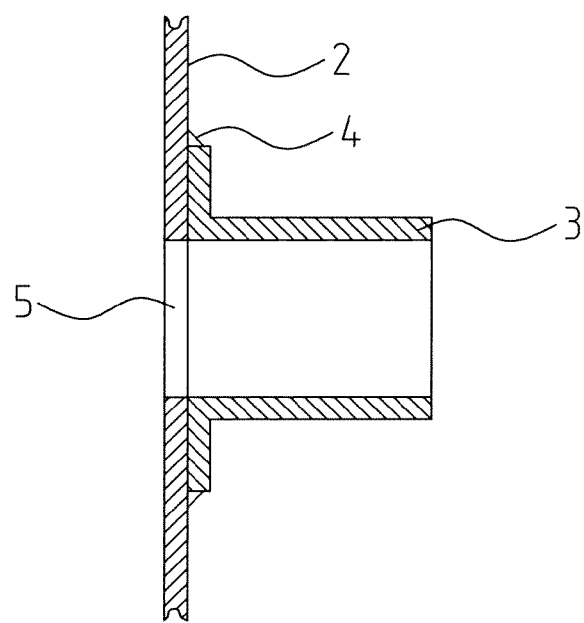
FIG. 3 is an exploded, enlarged cross-sectional view of the port showing one embodiment of means for connecting the port to the mattress.

Referring to FIG. 3, in one embodiment, the port comprises a flanged tube, attached to the cover, 2, by means of a weld, 4. The cover has a hole, 5, corresponding to the bore-hole of the tube.

Numerous other suitable means of attachment of the port to the cover will be obvious to those skilled in the art, and may include bulkhead threaded fittings, gasket fittings, and so on, allowing the port to be retro-fitted to existing mattress covers or covers of any cushioning device without requiring a welding apparatus.

Figure 4:
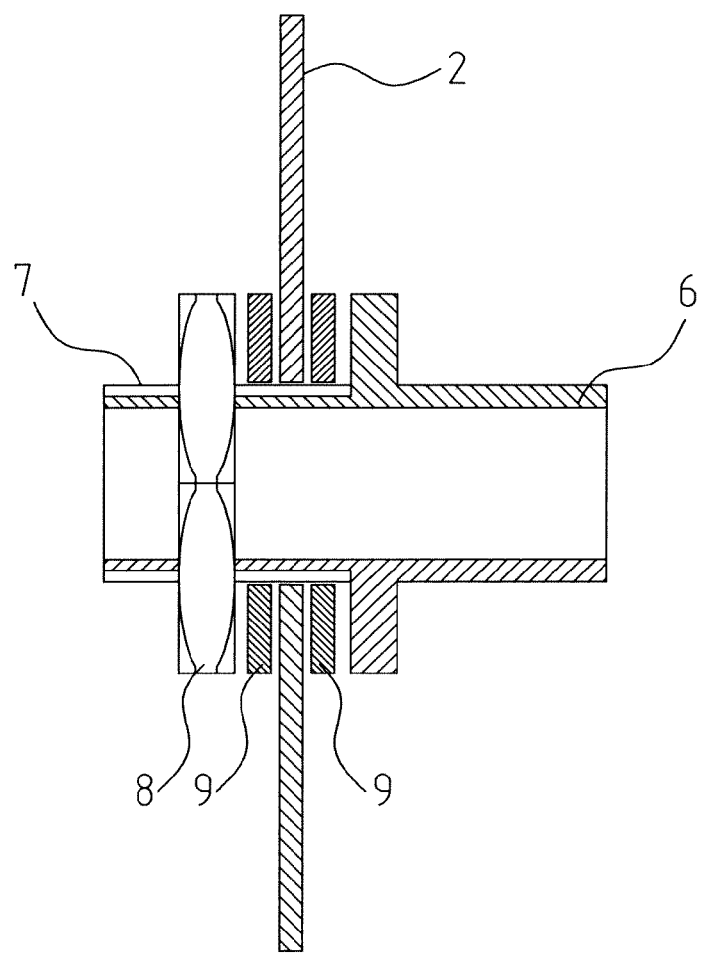
FIG. 4 is an alternative embodiment of means for connecting the port to the mattress.

An alternative embodiment is shown in FIG. 4. The cover 2, is punched with a hole. A nut 8, is fed through the hole, exploiting the elastic nature of the cover material to allow its passage through the relatively small hole. A flanged port tube 6, with a threaded section 7, is fed through the hole. Once again exploiting the flexibility of the cover, the nut is then tightened to the port, trapping the boundary of the hole between the nut and the port. Advantageously, one or more rubber gaskets 9, may be include in the assembly to aid sealing. Numerous existing technologies used for cable glands, for example, employ ratchets and other devices to ensure the nut does not loosen. Alternatively, numerous adhesives and adhesive tapes are available attaching the port to the cover.

Figure 5:
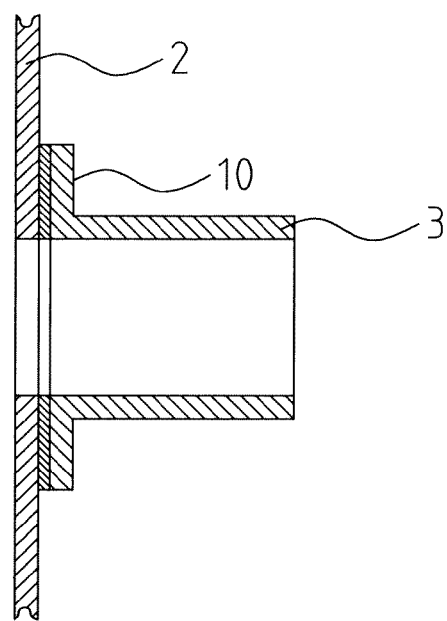
FIG. 5 is a further alternative embodiment of means for connecting the port to the mattress.

FIG. 5 shows another alternative embodiment, whereby the cover 2, is punched with a hole. A die-cut disc of double-sided self-adhesive tape 10, also with a hole, is placed over the hole in the cover. The port 3, is then affixed to the other side of the self-adhesive tape disc.

Figure 6:
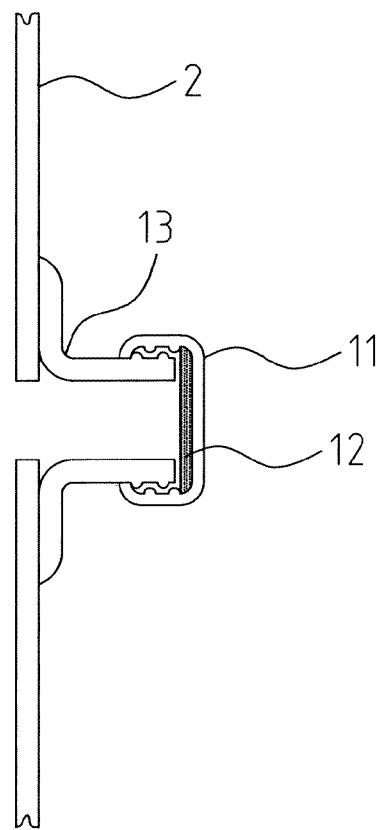
FIG. 6 is an exploded side view showing a further alternative embodiment in which the port is provided with a cap to prevent flow of air through the port when inspection is not taking place, i.e. when the port is not is use.

Advantageously, the port may be provided with a cap to prevent ingress or egress of air, when inspection of the interior is not taking place. Referring to FIG. 6, this may simply consist of a threaded cap 11, which screws onto a corresponding thread on the port 13. A seal, for example a rubber disc, may be provided within the cap to provide a seal when the cap is screwed tight.

Again, those skilled in the art will conceive numerous other ways of sealing or closing the port. Not exhaustively, these include bung or stopper, spigot or tap, pinch closure, pin-valve, Schrader-type valve, presta-type valve, shut-off coupling, and numerous other devices commonly found on camping-type air-mattresses (lilos), rubber dingies, and inflatable toys.

Advantageously, an arrangement may be provided whereby the port is normally in a sealed state, with no passage of air allowed, but passage of air is allowed when a suitable mating tube is offered to the port. Generically, these mechanisms are known as single shut-off or double shut-off couplings. A great many designs exist, and are commonly used in pneumatic and hydraulic applications, as well as in garden hose couplings, where the water is not allowed to flow when the mating coupling is detached.

Figure 7:
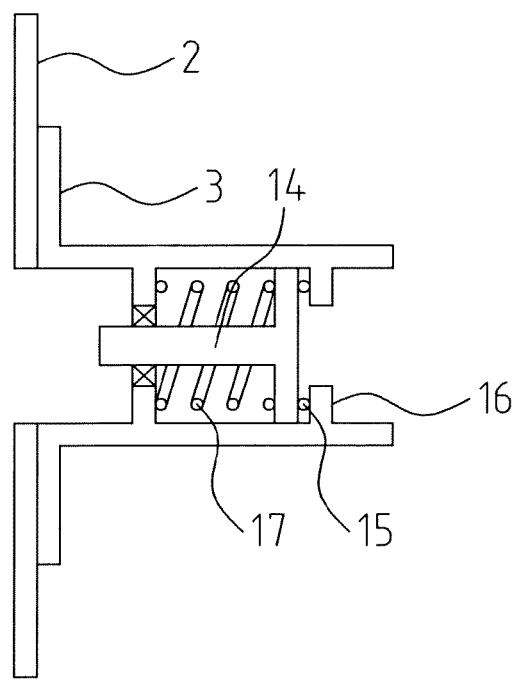
FIG. 7 is a side sectional view of a single shut-off coupling.

A simple example of a single shut-off coupling is shown in FIG. 7. The port contains interior shoulders 16, against which a plunger 14 is forced by a spring 17. Between the plunger and the shoulder is a seal 15. Only when a mating male part (comprising the terminal part of an air tube introduced to the assembly) is offered to push the plunger away from the shoulder, is air allowed to flow. When the male air tube is withdrawn, airflow is once again shut off. Numerous alternative and analogous mechanisms exist which may be appropriately applied.

According to the invention in the embodiments described hereinabove, means are provided for containing air within a mattress, until such time as inspection of the contents is made.

Upon inspection, it is not now necessary to unzip or otherwise open the whole mattress cover. The mattress interior may be accessed via the port, only when inspection is desired.

The inspection method of the present invention may include the step of inserting a swab into the port, to check for signs of microbial activity or decomposition.

The swab may be cultured to identify specific organisms such as MRSA or *Clostridium difficile*.

Alternatively, various bio-markers are commonly used to detect general microbial activity. For example, ATP (Adenosine triphosphate), is a multifunctional nucleoside triphosphate used in cells as a coenzyme. It exists wherever cellular metabolism is taking place, and is commonly measured to detect microbial activity, rot, putrefaction, or decomposition.

Numerous systems already exist which allow rapid measurement of ATP, often on a hand-held unit, without the need for culture media. One example is Systemsure Plus™, Hygiena 941 Avenida Acaso Camarillo, Calif. USA 93012. This gives the potential for swabbing the interior of the mattresses using a combined swab and reagent, then immediately checking for ATP, and thus detecting microbial activity within the mattress.

Advantageously, air may be extracted from the mattress to allow sampling of air from deeper within the mattress core. Whereas simple swabbing at the port entry will give information of contamination near the port, concentrations of ATP (or other indicator) may be higher elsewhere within the mattress. For example, if a mattress cover has been compromised, causing a leakage of body fluids into the mattress core, there may be a very virulent region of contamination close to the point of fluid ingress. Typically, this may be somewhere in the centre of the mattress, near the pelvic area of the patient. It is likely that ATP and other metabolic by-products will be concentrated in this area, and less so at the port. Therefore, it is advantageous to extract air from the port for sampling. This also has the advantage of testing for air-borne ATP or droplets containing ATP, rather than simply ATP aggregated on the mattress core surface inside the port.

Figure 8:
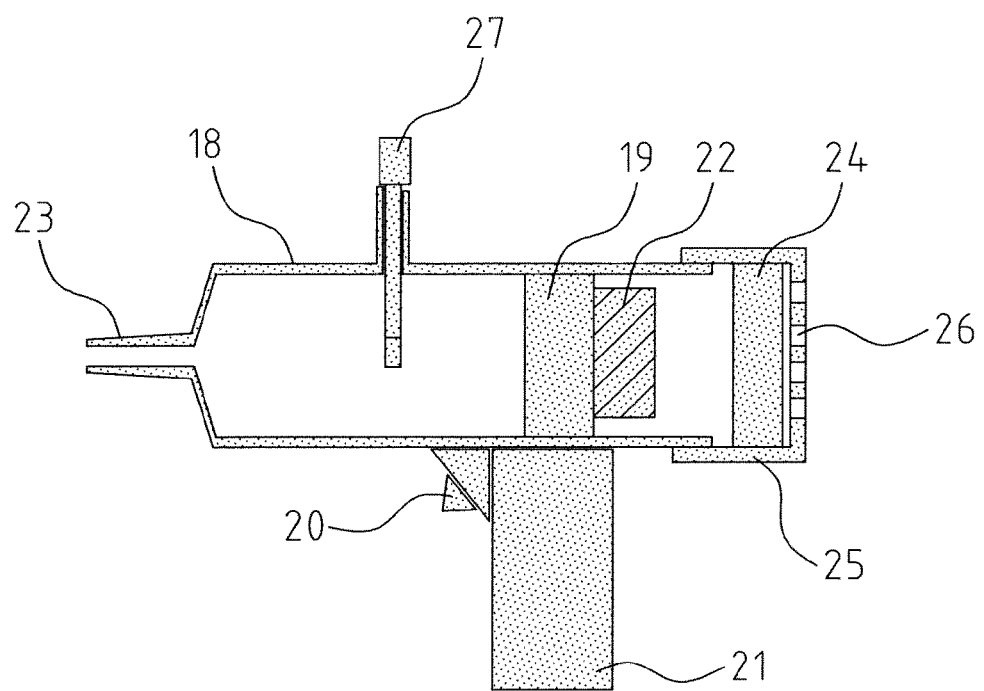
FIG. 8 is sectional view of a device for extracting and sampling air from the interior of a mattress including from deep within the mattress core.

FIG. 8 shows a suitable assembly for extracting and sampling air from the interior of the mattress. A casing, 18, contains a blower unit comprising a motor, 19, and a fan or impeller, 22. The blower is powered by a battery unit, 21, which may be contained within a handle, and activated by operating a switch, 20. A nozzle, 23, mates with the mattress port. As previously described, suitable arrangements may readily be provided whereby the application of the nozzle to the port opens the port and allows air to flow.

Air extracted from the mattress passes over the tip of a swab, 27, which is placed in a suitable opening in the chamber housing. Preferably the swab may be a combination swab with reagent to indicate ATP or other metabolyte. The swab may be removed and placed in an ATP analyser such as Systemsure Plus™, or other suitable device. Alternatively, the swab may be used for culture assay to identify microorganisms.

Various suitable methods and substances are available to detect and disclose the presence of pathogens.

One method of detecting the presence of pathogens is by monitoring changes in pH resulting from bacterial activity.

In accordance with the present invention, in one embodiment, the air extracted from the cushioning device may be passed over a single-use indicator strip or swab, impregnated with a pH-sensitive colourant capable of changing colour in the presence of one or more microorganisms. That is, the colourant may change from a first colour to a second colour or from colourless to a colour or from a colour to colourless. PH-sensitive indicators exist that are capable of differentiating between certain types of microorganisms. Bacteria, for example, may metabolize the growth medium and generate acidic compounds (e.g., $CO_2$) or alkaline compounds (e.g., ammonia) that lead to a change in pH. Likewise, certain microorganisms (e.g., bacteria) contain highly organised acid moieties on their cell walls. Because the acidic/basic shift may vary for different microorganisms, pH-sensitive colourants can be selected as appropriate for the desired pH transition so as to detect the presence of specific organisms.

Examples of such pH-sensitive colourants include: Phthalein colourants, many of which may be selected to give specific changes at specific pH values.

In an alternative embodiment of the invention, metal complexing can be used to detect and indicate the presence of microbes. For example, many microorganisms (e.g., bacteria and fungi) produce low molecular weight iron-complexing compounds in growth media, which are known as "siderophores." Metal complexing indicators may undergo a colour change in the presence of siderophores. Preferred metal complexing indicators include aromatic azo compounds, e.g. Eriochrome Black T, Eriochrome Blue SE, Eriochrome Blue Black B, Eriochrome Cyanine R, Xylenol Orange and many others.

In a further alternative embodiment of the invention, solvatochromatic colourants can be used to detect and indicate the presence of microbes. Solvatochromatic colourants change colour in the presence of a broad range of microorganisms. The colour change occurs as a result of changes in the polar environment. For example, a solvatochromatic colourant may be blue in a polar environment (e.g., water), but yellow or red in a non-polar environment (e.g., lipid-rich solution). Examples of suitable colourants are Merocyanine colourants, zwitterionic colourants (e.g. N-phenolate betaine colourants), or Reichardt's dye; 4-dicyanmethylene-2-methyl-6-(p-dimethylaminostyryl)-4H-pyran (DCM); 6-propionyl-2-(dimethylamino)naphthalene (PRODAN); 9-(diethylamino)-5H-benzo[a]phenox-azin-5-one (Nile Red); 4-(dicyanovinyl)julolidine (DCVJ); phenol blue; and many others, or mixtures thereof.

It should be understood that the present invention is not limited to any particular mechanism for the colour change. Even when a pH-sensitive colourant is employed, for instance, other mechanisms may actually be wholly or partially responsible for the colour change of the colourant. For example, redox reactions between the colourant and microorganism may contribute to the colour change.

In one embodiment of the present invention, the microbial detection means such as one of the colourants described above, is impregnated into the valve by mixing the microbial detection means with the oil referred to above, inside the valve. The valve can be in the form of a single self-adhesive valve for attachment to a mattress cover. In use, air is periodically expelled from the mattress, and all or some of this air must pass through the valve. The air, having been static within the mattress for some time, will be rich in any microbial metabolites, if any are present. If these are present in sufficiently large quantities, the colourant contained within the valve will change colour.

This colour change may be visible to the naked eye, or visible when illuminated by fluoroscopic or other methods.

The dye may be chosen to be sensitive to microbial activity in general, or specific categories of organism such as gram positive or gram negative bacteria.

In one embodiment, the microbial detection means associated with the valve comprises a two-part indicator means whereby: a first component microbial detection means such as a tablet composed of certain materials is included within the hermetically sealed infection control cushioning and/or bedding device; as a consequence of bacteriological or other microbial breakdown, an activator compound is released from the first component microbial detection means; the valve, including a second component microbial detection means such as an indicator substance which is specific to the activator compound included in the first compound and the indicator substance detects the presence of the activator which, in turn, indicates microbial presence within the hermetically sealed infection control cushioning and/or bedding device.

In this particular embodiment, the microbial detection means associated with the valve comprises a two-part indicator means wherein the first component microbial detection means is in the form of: a tablet composed of certain materials and this tablet is contained within the pillow or bedding; as a consequence of bacteriological or other microbial breakdown, a chemical compound X' is released; the valve contains an indicator substance which is specific to chemical compound X'; and the indicator substance detects the present of chemical compound X which, in turn, indicates microbial presence within the pillow or bedding.

Advantages of this system of detection are:

1. False positives are minimised, because the indicator is only sensitive to compound X, and compound X is only released within the pillow as a result of degradation of the tablet. Thus, the indicator is not sensitive to contaminants from the outside of the valve.

2. Whilst the indicator may be very specific to compound X, the conditions leading to the degradation of the tablet may be quite general if so desired. For example, degradation due simply to excessive moisture, or due to the action of a broad range of organisms, may lead to the breakdown of the tablet and so the release of compound X.

3. The system allows for the setting of a threshold level of biological activity, below which no indication will be made. For example, compound X may be contained within an inner layer of the tablet, and is released only when the outer layer is breeched by degradation.

Numerous pairs of substances may be used as the first component detection means including an activator material and second component detection means (an indicator), and many examples of such substances are described elsewhere. For example, a colloidal suspension of amylose (e.g. impregnated into a porous medium within the valve) would turn deep blue when exposed to iodine. Iodine is a solid, which sublimes in small quantities at room temperature. Thus, encapsulated in a biodegradable tablet, degradation of outer shell of the tablet would result in the evolution of small quantities of iodine gas. This gas, exhausting through the valve, would irreversibly activate the amylose indicator.

Many other pairs of such pairs of substances may be chosen to work in a similar way.

Examples using non-hazardous substances which can function as the first component detection means (activator compound) and second component detection means (indicators) include:

Benedict's solution (salts of sodium and copper), turning green in the presence of sugar. (Sugar released/dissolved/transported on breakdown of tablet).

Buiret solution (turning purple in the presence of certain proteins).

Sudan III, turning red in the presence of fat, eg vegetable oil.

Dichlorophenolindophenol, turning from blue to clear in the presence of vitamin C.

An effervescent vitamin C tablet could be used as our compound X tablet; and indeed many other substances could be used as the compound X.

Embodiments/variants:

1. Tablet of dry substance X contained within pillowcase. Indicator Y in valve. Excessive moisture/degradation causes solution and transport, or gas evolution of X.

2. Substance X is encapsulated within a tablet. One example may be a sugar-coating, as in Nurofen tablets. X is released when coating is breeched by degradation.

3. Substance X is distributed as a talc throughout the interior of the pillow. Moisture anywhere in the pillow causes solution, transport, or gas evolution of substance X.

4. Substance x is applied by spray or other means as a coating to the inside of the cover fabric.

5. Substance X may be preferentially located adjacent to the indicator valve.

6. Substance X may be preferentially located as an additional layer within the indicator valve, so that both of the stages of the 2-stage indication process take place within the valve.

The indicator may consist of a colour-changing material e.g. a leuco dye combined with a developing agent, such that the developing agent is specific to substance X, and produces a pH change to activate the leuco dye. Developing agents may be selected from phenolic resins or phenolic compounds such as 4-tert-butylphenol; 4-phenylphenol; methylene-bis(p-phenylphenol); 4-hydroxydiphenyl ether; alpha-naphthol; beta-napthol; methyl 4-hydroxybenzoate; benzyl 4-hydroxybenzoate; 4-hydroxydiphenyl sulfone; 4-hydroxyacetophenone; 2,2'-dihydroxydiphenyl; 4,4'-cyclohexylidenephenol; 4,4'-isopropylidenediphenol; 4,4-isopropylidenebis(2-methylphenol); a pyridine complex of zinc thiocyanate; 4,4-bis(4-hydroxyphenyl)valeric acid; hydroquinone; pyrogallol; phloroglucine; p-hydroxybenzoic acid; m-hydroxybenzoic acid; o-hydroxybenzoic acid; gallic acid; 1-hydroxy-2-naphthoic acid.

Advantageously, a cap, 25, may be provided at the rear exhaust side of the blower, comprising a filter, 24, and a perforated surface 26, to allow exhaust of sampled air. A suitable filter will allow air-flow, but retain microorganisms in the event of mattress contamination, thus preventing the spread of infection to the ambient atmosphere. As needed, the filter may be cleaned or replaced.

Figure 9:
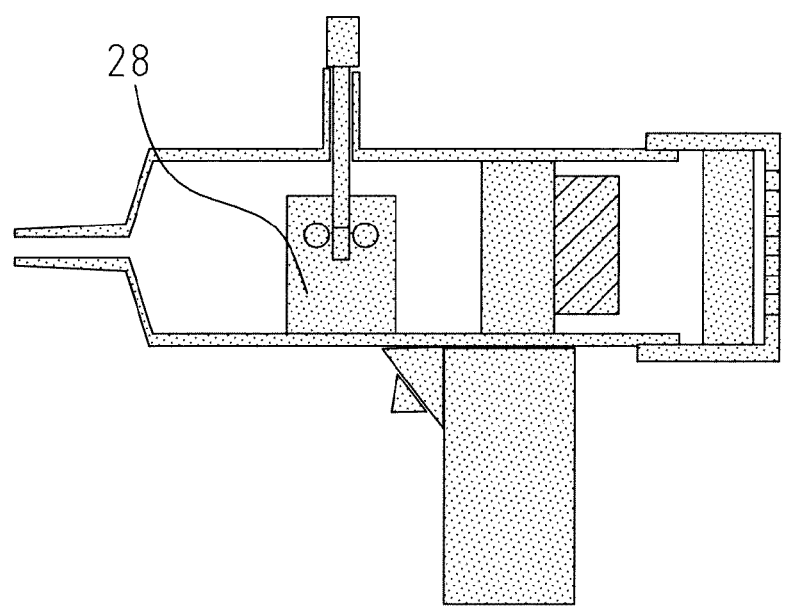
FIG. 9 is a side section view of an alternative embodiment of the air sampling device whereby an analyser is contained within a chamber of air sampling device.

FIG. 9 shows an embodiment whereby the analyser to detect the activation of the (e.g.) ATP reagent, is contained within the chamber of the air sampling device. This removes the step of removing the swab and placing it in a separate analyser.

Figure 10:
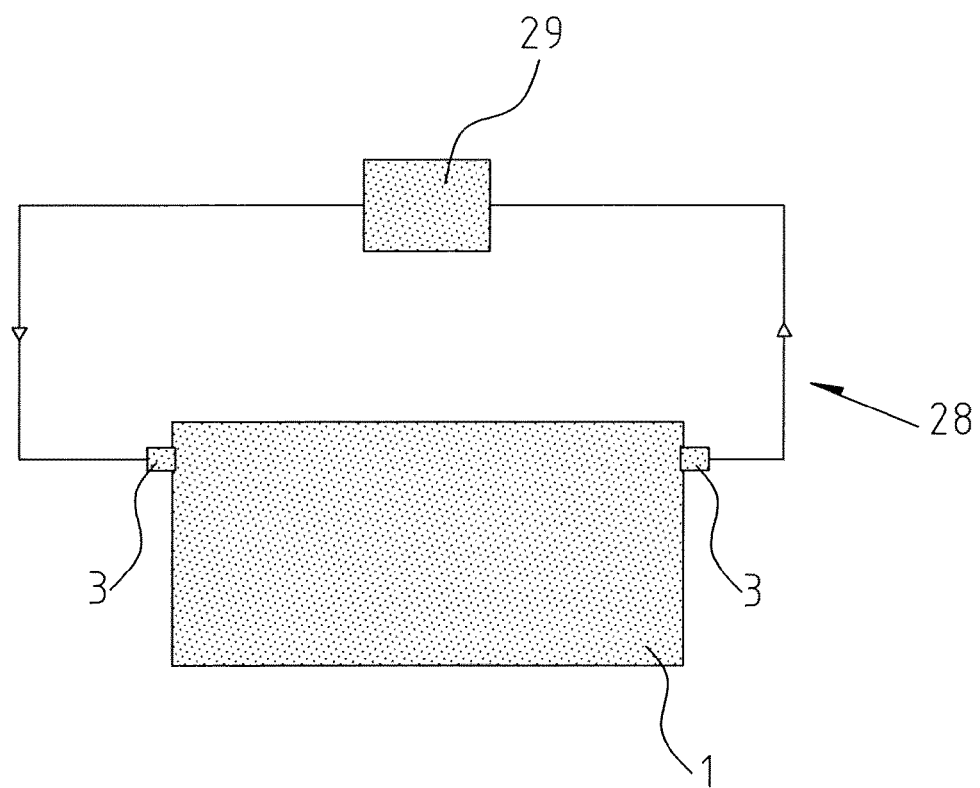
FIG. 10 is a schematic diagram of a closed loop system for returning sampled air taken from a first port in a mattress and returned to the mattress through a second port in the mattress.

Referring now to FIG. 10, in a further alternative embodiment, advantageously, two ports may be provided, one at either end of the mattress, and air sampled from one port returned to the other port. This has the advantage that the air passing through the air sampling device need not be filtered on exhaust, as it is simply being returned to the mattress. If the air is contaminated, it is returned to a mattress which is already contaminated. A further advantage is that the throughput of air from one side of the mattress to the other ensures that the entire mattress core is sampled.

FIG. 10 shows a schematic of this arrangement. In this case, the mattress, 1, has 2 ports, 3, which may be referred to as the "twin ports". The air sampler unit, 29, has a flexible tube one or both the inlet and the exhaust side. One end is connected to each mattress port, and air circulates through the tubing, 28, in the direction shown.

Figure 11:
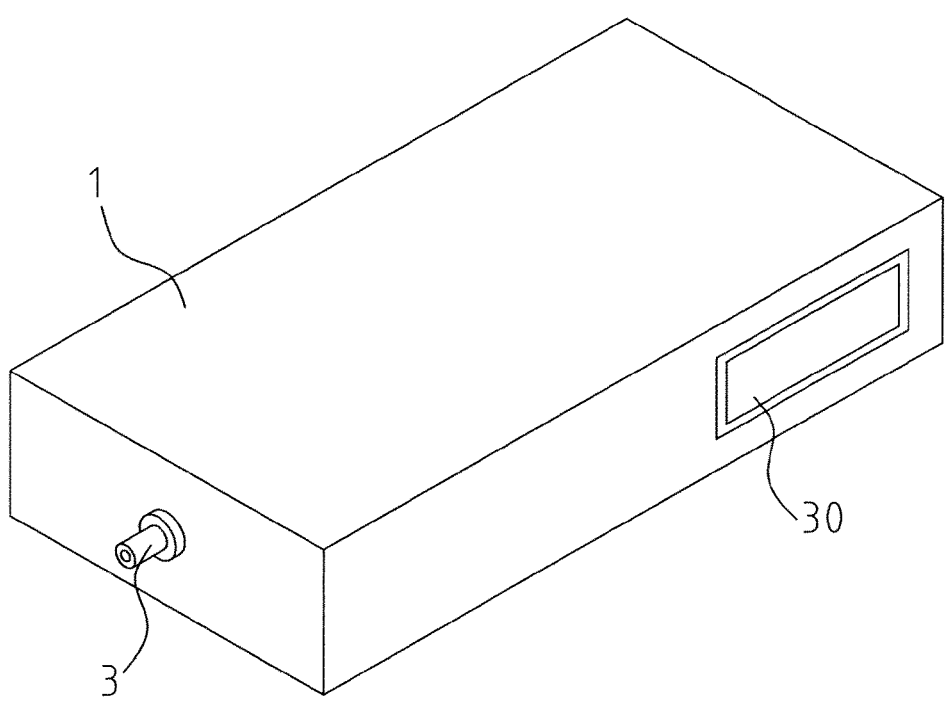
FIG. 11 is a perspective view of a preferred embodiment in which an air permeable microbial filter is included in the sealed mattress.

In a most preferred embodiment shown in FIG. 11, advantageously, the mattress cover is sealed by means of welding the seams, with no zip. This optimises the system, as contamination is prevented from entering the mattress if the cover is not damaged or otherwise compromised. In this embodiment, a membrane filter is advantageously applied to the cover, allowing air flow, but not allowing passage of micro-organisms or water. This not only allows the mattress to vent during normal operation without introducing contamination, but in the event of contamination reduced the occurrence of aerosolised contaminants being ejected from the mattress to the ambient atmosphere when the mattress is compressed. Such compression may occur for example when a patient gets on the bed, or redistributes weight on the mattress, or when the mattress is profiled into a different position on a profiling bed. Furthermore, the filter, insofar as it allows permeation of air, assists the air sampling device to extract air from the mattress, as replacement air is drawn through the membrane. In this case, the membrane is advantageously placed at the other end of the mattress from the port, so that air sampled from the port has been drawn through the length of the mattress, so sampling the mattress contents. FIG. 11 shows this arrangement, with the air-permeable microbial filter membrane, 30 attached to the mattress. An example of the application of the membrane would be a hole die-cut in the mattress cover, and then a membrane patch welded or affixed by other means so as to cover and seal the hole.

It will of course be understood that aspects of the present invention have been described by way of example only and it should be appreciated that additions and/or modifications may be made thereto without departing form the scope of the present invention as defined in the appended claims.

The invention claimed is:

1. A system for checking for interior air contamination, the system comprising:
a sealed device including a sealable port configured to allow extraction of air from an interior of the sealed device and further including a second sealable port;
means for extracting at least some of the air from the interior of the sealed device, the means for extracting comprising a sampling device including a pump unit; and
means for analyzing the extracted air to determine if it contains contaminants, the means for analyzing the extracted air comprising microbial detection means for indicating microbial presence;
wherein the sealable port and the second sealable port comprise twin ports removably engageable with the sampling device to allow a circuit of air between the pump unit and the sealed device, such that air extracted from one of the twin ports by the pump unit is returned to the other of the twin ports, allowing no escape of the air to the environment, and
wherein the sealed device is sealed to prevent, except through the sealable port, exterior air to flow into the sealed device and the air from the interior to flow out.

2. A system as in claim 1, wherein the sealed device is sealed by an occlusive cover and welded seams.

3. A system as in claim 2, wherein the sealed device is provided with a vent comprising a microbial filter to allow passage of the external air but not passage of microbes, to replenish the air within the sealed device.

4. A system as in claim 1, wherein the microbial detection means includes at least one of the following group: a microbial detection reagent; a pH-sensitive colourant; metal complexes; and solvatochromatic colourants.

5. A system as in claim 1, wherein the microbial detection means comprises a first component contained within the sealed device and a second component on an exterior of the sealed device the first component comprising an activator material which is at least one of releasable and degradable as a consequence of degradation, and the second component comprising an indicator configured to detect the activator material released from the first component.

6. A system as in claim 1, wherein the air from the interior of the sealed device is actively sampled by the sampling device.

7. A system as in claim 6, wherein the sampling device comprises means for directing the actively sampled air over an indicator strip impregnated with indicators configured to indicate contamination.

8. A system as in claim 6, wherein the sampling device comprises means for directing the actively sampled air over a swab for subsequent at least one of culture and analysis.

9. A system as in claim 6, wherein the sampling device is configured to perform real-time analysis of metabolites.

10. A system as in claim 1, wherein air extracted from the sealed device is stored for later analysis using at least one of a chemical analyzer, swabs, and culture plates.

11. A method for sampling air from the interior of a device, the method comprising:
sealably coupling a sampling device and twin ports of a sealed device having air in an interior thereof, the twin ports including a sealable port and a second sealable port, wherein the sealed device is sealed to prevent, except through the twin ports, air to flow into the sealed device and the air from the interior to flow out;
extracting, with means for extracting comprising a sampling device including a pump unit, at least some of the air from the interior of the sealed device; and
exposing the extracted air to means for analyzing the extracted air, the means for analyzing the extracted air comprising microbial detection means in the sampling device for indicating microbial presence,
wherein the twin ports are removably engageable with the sampling device to allow a circuit of air between the pump unit and the sealed device, such that air extracted from one of the twin ports by the pump unit is returned to the other of the twin ports, allowing no escape of the air to the environment.

12. A method as in claim 11, further comprising measuring adenosine triphosphate to detect microbial activity in the extracted air.

13. A method as in claim 11, further comprising testing the extracted air in real time using an analyser to detect presence of at least one of microbes and chemical indicators of microbes.

14. A method as in claim 11, further comprising storing the extracted air for later analysis using at least one of a chemical analyser, swabs, and culture plates.

15. A method as in claim 11, wherein the microbial detection means comprises a collection swab.

16. A method as in claim 11, further comprising filtering the extracted air to remove contaminants.

17. A method as in claim 11, wherein the sealed device includes a vent comprising a filter configured to allow ingress of air and restrict ingress of microbes.

18. A system for checking for interior air contamination, the system comprising:

a sealed device including twin sealable ports configured to allow extraction of air from an interior of the sealed device;
a pump to extract at least some of the air from the interior of the sealed device; and
a microbial detector to indicate the presence of microbes,
wherein the twin sealable ports are removably engageable with the sampling device to allow a circuit of air between the pump and the sealed device, such that air extracted from one of the twin ports by the pump is returned to the other of the twin ports, allowing no escape of the air to the environment, and
wherein the sealed device is sealed to prevent, except through the twin sealable ports, air to flow into the sealed device and the air from the interior to flow out.

19. A system as in claim 18, wherein the sealed device is sealed by an occlusive cover and welded seams.

20. A system as in claim 18, wherein the microbial detector includes at least one of the following group: a microbial detection reagent; a pH-sensitive colourant; metal complexes; and solvatochromatic colourants.

21. A system as in claim 18, wherein the microbial detector comprises a first component contained within the sealed device and a second component on an exterior of the sealed device, the first component comprising an activator material which is at least one of releasable and degradable as a consequence of degradation, and the second component comprising an indicator configured to detect the activator material released from the first component.

22. A system as in claim 18, further comprising a sampling device, wherein the air from the interior of the sealed device is actively sampled by the sampling device.

23. A system as in claim 22, wherein the sampling device comprises means for directing the actively sampled air over an indicator strip impregnated with indicators configured to indicate contamination.

24. A system as in claim 22, wherein the sampling device comprises means for directing the actively sampled air over a swab for subsequent at least one of culture and analysis.

25. A system as in claim 22, wherein the sampling device is configured to perform real-time analysis of metabolites.

* * * * *